(12) United States Patent
Tauch et al.

(10) Patent No.: US 7,674,736 B2
(45) Date of Patent: Mar. 9, 2010

(54) GLASS FOR DENTAL APPLICATIONS

(75) Inventors: Diana Tauch, Mels (CH); Harald Bürke, Frastanz (AT); Volker M. Rheinberger, Vaduz (LI)

(73) Assignee: Ivoclar Vivadent, AG, Schaan (LI)

( * ) Notice: Subject to any disclaimer, the term of this patent is extended or adjusted under 35 U.S.C. 154(b) by 0 days.

(21) Appl. No.: 11/798,172

(22) Filed: May 10, 2007

(65) Prior Publication Data

US 2008/0081103 A1 Apr. 3, 2008

(30) Foreign Application Priority Data

Sep. 29, 2006 (EP) .................................. 06020553

(51) Int. Cl.
| | |
|---|---|
| *C03C 3/085* | (2006.01) |
| *C03C 3/089* | (2006.01) |
| *C03C 3/091* | (2006.01) |
| *C03C 3/093* | (2006.01) |
| *C03C 3/083* | (2006.01) |
| *C03C 3/087* | (2006.01) |
| *B05D 3/04* | (2006.01) |

(52) U.S. Cl. ............................. 501/69; 501/65; 501/66; 501/67; 501/68; 501/70; 427/376.2

(58) Field of Classification Search .................. 501/54, 501/69, 65, 66, 67, 68, 70, 72, 5, 6, 7; 427/376.2; 106/35

See application file for complete search history.

(56) References Cited

U.S. PATENT DOCUMENTS

| | | | |
|---|---|---|---|
| 5,281,563 A | 1/1994 | Komma et al. | |
| 5,432,130 A | 7/1995 | Rheinberger et al. | |
| 5,618,763 A * | 4/1997 | Frank et al. | ..................... 501/5 |
| 5,641,347 A * | 6/1997 | Grabowski et al. | ............ 106/35 |
| 6,120,591 A | 9/2000 | Brodkin et al. | |
| 6,155,830 A | 12/2000 | Brodkin et al. | |
| 6,206,958 B1 * | 3/2001 | Panzera et al. | ................ 106/35 |
| 6,606,884 B2 * | 8/2003 | Schweiger et al. | ........... 65/17.6 |
| 6,645,285 B2 * | 11/2003 | Brodkin et al. | ............... 106/35 |
| 2003/0122270 A1 * | 7/2003 | Brodkin et al. | ............... 264/16 |
| 2005/0098064 A1 | 5/2005 | Schweiger et al. | |
| 2005/0277539 A1 | 12/2005 | Assmann et al. | |

FOREIGN PATENT DOCUMENTS

| | | |
|---|---|---|
| DE | 103 36 913 A1 | 3/2005 |
| EP | 0 544 145 B1 | 6/1993 |
| EP | 0 695 726 B1 | 4/1997 |
| EP | 0 622 342 B1 | 8/1998 |
| EP | 0 827 941 B1 | 11/1999 |
| EP | 1 170 261 A1 | 1/2002 |
| EP | 0 885 606 B1 | 7/2003 |
| EP | 1 329 430 A2 | 7/2003 |
| EP | 1 167 311 B1 | 4/2004 |
| EP | 1 452 500 A1 | 9/2004 |
| WO | 99/45888 | 9/1999 |

* cited by examiner

*Primary Examiner*—Jerry Lorengo
*Assistant Examiner*—Noah S Wiese
(74) *Attorney, Agent, or Firm*—George R. McGuire; Ann M. Knab; Bond Schoeneck & King, PLLC

(57) ABSTRACT

The invention relates to a glass for dental applications which can be used as a glazing material of dental restorations and resists high temperatures, and thus does not tend to flow.

39 Claims, No Drawings

GLASS FOR DENTAL APPLICATIONS

The present application claims priority, pursuant to 35 U.S.C. §119 to European Application No. 06020553.1 filed Sep. 29, 2006, the entire contents of which are incorporated herein by reference.

FIELD

The invention relates to a glass for dental applications, such as glasses which has a low coefficient of thermal expansion and a high stability upon firing and is outstandingly suitable as a glaze material for dental restorations.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

In dentistry, in addition to metal-supported restorations, all-ceramic restorations are increasingly used. Frameworks made of metal or ceramics are usually provided with several layers of coating and veneering materials to achieve aesthetically particularly attractive restorations.

In the processing of ceramic frameworks a process has now been established in which, irrespective whether using the layering technique or staining technique, a separate glaze firing takes place at high temperatures. In addition to the achieving an optically attractive gloss, the resulting glaze also has the task of equalizing possible unevennesses of the surface and thus reducing the formation of plaque. However, the application of this glaze represents not only a further working step but also an additional thermal stress placed on the dental restoration.

Many different glass-ceramics are known from the state of the art which are suitable as framework material for dental restorations. In recent years, a heat-pressing technique (e.g., IPS Empress® from Ivoclar Vivadent AG, Schaan, Liechtenstein) has been joined by mechanical processing in CAD/CAM systems for the preparation of such frameworks. In particular the CEREC® system from Sirona has found many users worldwide.

Furthermore, glass-ceramics are known from the state of the art which are present in a first crystallization stage for simple mechanical processing, and are subsequently subjected to a further crystallization, also called ceramization, in order to improve the mechanical properties of the framework of the dental restoration. Examples of such framework materials are mica glass-ceramics or lithium silicate glass-ceramics which are mechanically processed in the metasilicate phase and then form the lithium disilicate phase through a further ceramization having a greater strength. Such glass-ceramics are described in detail in DE 103 36 913.

In recent years different grades of stabilized $ZrO_2$ ceramics have found use in dental laboratories and in dental practices. Depending on the degree of sintering in each case, i.e., partly or completely densified materials, different machine and processing systems have become established on the market.

To achieve an aesthetic appearance corresponding to the natural tooth, such ceramic or metallic frameworks are veneered with several layers of glass-ceramics or glasses and finally sealed with a glaze.

There are, however, a series of starting materials with which it is not necessary to simulate the appearance of the natural tooth by the additional application of several layers. Multi-colored blanks for CAD/CAM processing, such as are marketed by Vita under the name Trilux®, are examples of such materials. It is to be assumed that interest in such starting materials will soon increase strongly because an immense amount of time can be saved in the preparation of dental restorations.

It is also possible to process suitably colored starting materials if the restoration prepared from these is not directly visible, such as inlays or onlays in the side-tooth area. These restorations allow the possibility to finalize dental processing with just a glaze.

However, it has now also been shown that materials are increasingly being used which, for easier workability, are processed by means of CAD/CAM in a state in which the highest strength has not yet been reached. After milling or grinding, a further crystallization is triggered by thermal treatment and thus the mechanical properties are improved. If the customary veneering and layering materials are also used, a separate firing is necessary for the desired glaze as the known veneering and layering materials lack the required stability upon firing. However, these customary materials also lack the required dimensional stability at the high temperatures used for firing. This manifests itself in that these materials begin to flow.

SUMMARY

According to one aspect of the invention, a material with which a glaze can be produced on a dental restoration and which has a high dimensional stability upon firing is provided. In addition, according to a further aspect, the processing of this material to form a glaze is effected simultaneously with the formation of crystals in a restoration, thus the working steps of the (a) final ceramization or crystallization and of the (b) glaze firing, can be carried out in one step.

According to a further aspect, there is provided a glass comprising the following components, in weight percent:

| | |
|---|---|
| $SiO_2$ | 60.0-65.0 |
| $K_2O$ | 15.0-19.0 |
| $Al_2O_3$ | 6.0-10.5 |
| $Li_2O$ | 1.8-2.2 |
| $Me^{II}O$ | 2.5-8.5 |
| further oxides | 1.5-7.0 | wherein
(a) $Me^{II}O$ represents at least one divalent oxide which is selected from the group of the oxides of Ca, Mg, Sr and Zn, and
(b) further oxides represents at least one oxide which is selected from the group of the oxides of B, Zr, Ce and Y.

According to further aspects of the present invention, there are provided a glazing material, optionally combined with a dental restoration, comprising the above-described glass.

According to yet another aspect, the present invention provides a method of applying a glaze onto a dental restoration, the method comprising:
(a) applying the glass composed as described above onto the dental restoration; and (b) thermally treating the dental restoration and the applied glass in a manner which transforms the glass into a glaze that adheres firmly to the restoration.

DETAILED DESCRIPTION

A glass according to the invention for dental applications can comprise the following components:

| Component | wt.-% |
|---|---|
| $SiO_2$ | 60.0-65.0 |
| $K_2O$ | 15.0-19.0 |
| $Al_2O_3$ | 6.0-10.5 |
| $Li_2O$ | 1.8-2.2 |
| $Me^{II}O$ | 2.5-8.5 |
| further oxides | 1.5-7.0 | wherein
(a) $Me^{II}O$ represents at least one divalent oxide which is selected from the group of the oxides of Ca, Mg, Sr and Zn, and
(b) further oxides represents at least one oxide which is selected from the group of the oxides of B, Zr, Ce and Y.

The glass may essentially consist of the above-identified components.

Further, the glass may comprise at least one of the components in the following amount(s):

| Component | wt.-% |
|---|---|
| $SiO_2$ | 63.0-65.0 |
| $K_2O$ | 17.5-19.0 |
| $Al_2O_3$ | 9.5-10.5 |
| $Li_2O$ | 1.9-2.1 |
| $Me^{II}O$ | 4.5-7.5 |
| further oxides | 2.5-6.0 |

It has also been proven advantageous that the glass comprises less than 2.0 wt.-% ZnO.

Further, a glass which comprise 0.5 to 2.5 wt.-% $ZrO_2$ is encompassed by the present invention.

In a further embodiment, the glass comprises 15.5 to 19.0, in particular 17.5 to 19.0 wt.-% $K_2O$.

According to a further embodiment of the present invention, the glass may comprise at least one of the components in the following amount(s):

| Component | wt.-% |
|---|---|
| $SiO_2$ | 64.0-65.0 |
| $K_2O$ | 18.0-18.5 |
| $Al_2O_3$ | 10.0-10.5 |
| $Li_2O$ | 2.0-2.1 |
| MgO | 0.4-2.1, in particular 0.4-0.7 |
| CaO | 1.9-2.3, in particular 1.9-2.1 |
| $ZrO_2$ | 1.0-2.4, in particular 2.0-2.4 |
| $CeO_2$ | 0.4-0.8 |

The glass according to the invention surprisingly proves dimensionally stable at the high temperatures which are used for a simultaneous crystal formation of a suitable dental restoration. Thus the final ceramization of a suitable framework material can take place simultaneously with the desired application of a glaze in one step. This represents an enormous advantage to the user.

The use of the glass according to the invention is particularly advantageous on restoration parts which have been ground or milled in an only partial strengthened state and are then subjected to a further thermal treatment in order to improve the mechanical properties. In particular, the use of the glass is suitable as glaze on restoration parts from a lithium metasilicate glass-ceramic which forms lithium disilicate crystals as a result of the thermal treatment.

Further, the glass according to the invention preferably has a firing temperature of 900 to 950° C., in particular of 910 to 930° C. The firing temperature is determined in the manner given in the examples.

In addition, the glass according to the invention does not react with the framework material and, after the thermal treatment, provides it with an aesthetic high gloss. It also possesses a very good chemical stability. This is an important property for materials which constantly come into contact with various fluids in the oral cavity.

When used as glaze material for a restoration based on a glass or a glass-ceramic, the coefficient of thermal expansion of the glass according to the invention can be suitably adapted by varying the type and amount of the components present in the glass. A glass is preferred which has a linear coefficient of thermal expansion of 8.0 to $9.5 \times 10^{-6}$ $K^{-1}$ and in particular of 8.4 to $9.1 \times 10^{-6}$ $K^{-1}$ in the temperature range of 100 to 500° C.

The glass according to the invention can be prepared according to the processes known from the state of the art by forming a glass melt at temperatures of about 1200° C. to about 1600° C. from suitable starting materials such as oxides, hydroxides and carbonates.

The glass melt is then usually poured into water and the glass granules formed are reduced to a particle size of at most 100 μm, preferably at most 50 μm.

The glass according to the invention can be used in particular as glazing material of a dental restoration and the invention is also directed to this method of use.

The dental restoration can be a bridge, a crown, an inlay, an onlay, a veneer or a cap, or a part thereof.

The dental restoration can be based on a glass, a ceramic, a metal or a glass-ceramic and in particular based on a glass-ceramic.

Lithium silicate glass-ceramic, a mica glass-ceramic or a chondrodite glass-ceramic can be used as glass-ceramic. These can be prepared from suitable precursors which after the application of the glass according to the invention as glaze show a strong increase in strength and lead to the formation of the desired glass-ceramic as a result of the thermal treatment and the crystal formation triggered thereby.

The lithium silicate glass-ceramic can comprise a lithium metasilicate or a lithium disilicate glass-ceramic.

When using a lithium metasilicate glass-ceramic as precursor the thermal treatment leads to the transformation of the metasilicate crystals into disilicate crystals, whereby the structure is greatly strengthened.

The invention also relates to a process for applying a glaze to a dental restoration in which:
(a) the glass comprising a composition of the present invention is applied onto the dental restoration; and
(b) the dental restoration provided with the glass is subjected to a thermal treatment in order to transform the glass into a glaze which adheres firmly to the restoration.

The thermal treatment preferably takes place at a temperature of at least 860° C., in particular at 860 to 960° C.

As already mentioned, a dental restoration based on a glass, a ceramic, a metal or a glass-ceramic is used in particular.

The thermal treatment may also lead to the formation of crystals in the glass or the glass-ceramic. By formation of crystals is also meant the transformation of crystals, e.g., transformation of metasilicate into disilicate crystals.

The glass according to the invention not only offers great advantages when used in processes for applying a glaze to lithium silicate glass-ceramics but can also be used in an advantageous manner in other glass-ceramic materials which precipitate different crystal phases depending on the thermal treatment used. Examples of such other glass-ceramic materials are given in K. Chyung, G. H. Beall, D. G. Grossman; Fluorophlogopite Mica Glass-Ceramics; 10th Int. Cong. on Glass, Kyoto, The Ceramic Soc. Japan 14 (1974) 33-40.

In a process performed according to the invention glasses or glass-ceramics can be used which can form lithium disilicate crystals or mica crystals during the thermal treatment. Therefore in step (a) a restoration based on lithium metasilicate glass-ceramic or chondrodite glass-ceramic may be used.

Further, a process of the present invention that leads to the formation of crystals brings about an increase in the strength, in particular the bending strength, of the dental restoration.

The invention is described in further detail below with reference to illustrative, non-limiting examples:

EXAMPLES

Example 1 to 4

Composition and Properties of Glasses According to the Invention

A total of 4 different glasses according to the invention were prepared having the chemical compositions given in the following table:

TABLE 1

Composition of glasses according to the invention (values in wt.-%)

| Component | Example 1 | Example 2 | Example 3 | Example 4 |
| --- | --- | --- | --- | --- |
| $SiO_2$ | 60.69 | 64.46 | 64.86 | 61.57 |
| $K_2O$ | 16.63 | 18.20 | 18.31 | 15.78 |
| $Al_2O_3$ | 6.53 | 10.07 | 8.05 | 6.20 |
| $Li_2O$ | 2.11 | 2.01 | 2.03 | 2.00 |
| MgO | 0.53 | 0.54 | 2.01 | 0.50 |
| CaO | 2.27 | 2.01 | 2.03 | 2.15 |
| SrO | 2.11 | — | — | 2.00 |
| ZnO | 3.16 | — | — | 3.00 |
| $B_2O_3$ | — | — | — | 1.13 |
| $ZrO_2$ | 1.05 | 2.16 | 2.17 | 1.00 |
| $CeO_2$ | 0.71 | 0.54 | 0.54 | 0.67 |
| $Y_2O_3$ | 4.22 | — | — | 4.00 |

For their preparation, in each case, a mixture of suitable oxides, hydroxides and carbonates was melted in a platinum/rhodium crucible at a temperature of 1500° C. to 1550° C. over a homogenization time of 1 to 1.5 hours. The glass melt was quenched in water and ground to an average particle size of less than 100 µm, relative to the number of particles.

Selected properties measured using suitable testpieces made from the respective glass are given in Table 2 for the glasses from Table 1. The examples illustrate that glasses with the desired properties can be prepared by varying the components and their amounts in the given ranges.

TABLE 2

Properties of glasses according to the invention

| Example No. | Firing temperature | Coefficient of expansion (100-500° C.) | Chemical stability | Vickers hardness HV5 |
| --- | --- | --- | --- | --- |
| 1 | 910° C. | $8.95 \times 10^{-6} K{-1}$ | 1 µg/cm$^2$ | 5463 MPa |
| 2 | 930° C. | $8.87 \times 10^{-6} K{-1}$ | 6 µg/cm$^2$ | 5804 MPa |
| 3 | 930° C. | $9.07 \times 10^{-6} K{-1}$ | 3 µg/cm$^2$ | 5382 MPa |
| 4 | 920° C. | $8.44 \times 10^{-6} K{-1}$ | 8 µg/cm$^2$ | 5310 MPa |

These properties were measured in the manner described below using the cited standards:

Measuring the Firing Temperature

The firing temperature was measured using platelets with a diameter of 12 mm and a height of 2 mm which were prepared according to DIN ISO 6872. These platelets were fired at different temperatures and then the degree of firing was assessed using the criteria of number of bubbles, surface gloss and edge rounding.

Measuring the Coefficient of Expansion α

To measure the linear coefficient of thermal expansion a according to ISO 6872, a rod-shaped green body which was sintered in a vacuum furnace at a heating-up rate of 60° C./min and with a holding time of 1 min at the firing temperature given in Table 2 to prepare the testpiece was prepared from the powder of the respective glass. The linear coefficient of thermal expansion was then measured in the range of 100° C. to 500° C. using the thus-obtained testpieces.

Measuring the Chemical Stability

The acid resistance is a measure of the chemical resistance of the very glasses used in dentistry, as these are permanently exposed to the action of acid substances in the oral cavity.

Acid resistance was measured according to ISO 6872 (1995). To this end, firstly test platelets with a diameter of 12 mm and a thickness of 1 mm were prepared by sintering together the glass powder with an average particle size of less than 50 µm. The powder was kept for 1 minute at the respective firing temperature to prepare the testpieces. The test platelets were then treated for 16 hours with 4 vol.-% aqueous acetic acid at 80° C. The loss of mass which occurred was then measured in relation to the surface of the testpiece platelets as a measure of the acid resistance.

Measuring the Vickers Hardness

Hardness is a measure of the mechanical resistance of materials. As the glasses used are exposed to wear by chewing forces it is advisable to quantify this property.

To measure Vickers hardness, testpieces with a diameter of 20 mm and a thickness of 3 mm were prepared by sintering together the glass powder with an average particle size of less than 50 µm. The powder was kept for 1 minute at the respective firing temperature to prepare the testpieces. The Vickers hardness was measured according to ISO 14705 (2000) by using the average value from 6 measurements taken on polished surfaces.

Example 5

Use of Glass According to the Invention as Glaze Material

This example describes the use of the glass according to the invention as glaze material for restoration parts which have been ground or milled in an only partially strengthened state and which subsequently are subjected to a further thermal treatment in order to improve the mechanical properties. A restoration of a lithium metasilicate glass-ceramic was used. Surprisingly the one step thermal treatment led not only to a clear increase in strength, but simultaneously also to the glazing of the restoration. The glass according to the invention can thus be described as instant glazing material.

Glass powder according to example 2 with an average particle size of at most 50 µm was mixed with a universal glaze and staining dye from Ivoclar Vivadent AG and applied in an average layer thickness of about 150 µm to a lithium metasilicate glass-ceramic model crown prepared by means of CAD/CAM technology (Cerec® 3 from Sirona, Bensheim, Germany). The thermal treatment then took place at a temperature of 860° C. at a heating-up rate of 60° C./min and with a holding time of 10 min. The lithium metasilicate glass-ceramic was transformed into a lithium disilicate glass-ceramic and the glaze firing with the glass according to the invention took place at the same time.

Studies of the strength of the glass-ceramic used and obtained after the thermal treatment (biaxial bending strength) produced the following results (average value from 4 measurements taken by using unglazed testpieces):

| Lithium metasilicate glass-ceramic: | 244 ± 27 MPa |
|---|---|
| Lithium disilicate glass-ceramic: | 537 ± 41 MPa |

Furthermore the glossiness of an unglazed testpiece and one lithium disilicate glass-ceramic testpiece glazed with the glass according to the invention was measured (average value of 2 testpieces and 4 measurements each):

| Lithium disilicate glass-ceramic (unglazed): | 5% |
|---|---|
| Lithium disilicate glass-ceramic (glazed): | 60% |

The gloss was measured with the novo-curve from Rhopoint, Great Britain, which allows a measurement of the glossiness of even small samples. Measurement took place according to the standard ISO 2813. The measurement principle is that a light beam is directed onto the surface of the testpiece at an angle of 60° and the intensity of the reflected light is measured in the equipment and compared with a reference value.

Example 6

This example describes the use of the glass according to the invention as glazing material for a mica glass-ceramic.

For this, a glass block made of a glass which is capable of precipitating mica crystals was annealed at a temperature of 750° C. for 1 hour. Chondrodite crystals were precipitated in the glass by volume crystallization with this treatment. The glass-ceramic was still workable with diamond tools in this state. A model crown was prepared from this by means of CAD/CAM technology (Cerec® 3 from Sirona, Bensheim, Germany).

Glass powder according to example 1 with an average particle size of at most 50 µm was mixed with a universal glaze and staining dye from Ivoclar Vivadent AG and applied to the model crown in an average layer thickness of about 150 µm. Thermal treatment followed at a temperature of 950° C. with a heating-up rate of 60° C./min and a holding time of 20 min. The chondrodite glass-ceramic was thereby transformed into a mica glass-ceramic and the glaze firing took place at the same time with the glass according to the invention.

Studies of the strength (biaxial bending strength) produced the following results (average value from 4 measurements taken on unglazed testpieces):

| Chondrodite glass-ceramic: | 150 +/− 22 MPa |
|---|---|
| Mica glass-ceramic: | 310 +/− 42 MPa |

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A composition consisting of a glass comprising the following components, in weight percent:

| $SiO_2$ | 60.0-65.0% |
|---|---|
| $K_2O$ | 15.0-19.0% |
| $Al_2O_3$ | 6.0-10.5% |
| $Li_2O$ | 1.8-2.2% |
| $Me^{II}O$ | 2.5-8.5% |
| further oxides | 1.5-7.0% | wherein
(a) Me"O represents at least one divalent oxide which is selected from the group of the oxides of Ca, Mg, Sr and Zn, wherein ZnO is present in an amount less than 2.0%, and
(b) further oxides represents at least one oxide which is selected from the group of the oxides of B, Zr, Ce and Y; and
wherein the glass has a linear coefficient of thermal expansion of 8.0 to 9.5×10$^{-6}$ K$^{-1}$ in the temperature range of 100 to 500° C.

2. The composition according to claim 1, wherein the glass essentially consists of the components.

3. The composition according to claim 1, wherein the glass comprises at least one of the components in the following quantity(s), in weight percent:

| $SiO_2$ | 63.0-65.0% |
|---|---|
| $K_2O$ | 17.0-19.0% |
| $Al_2O_3$ | 9.5-10.5% |
| $Li_2O$ | 1.9-2.1% |
| $Me^{II}O$ | 4.5-7.5% |
| further oxides | 2.5-6.0%. |

4. The composition according to claim 1, wherein the glass further comprises 0.5 to 2.5 wt.-% $ZrO_2$.

5. The composition according to claim 1, wherein the glass further comprises 15.5 to 19.0 wt.-% $K_2O$.

6. The composition according to claim 5, wherein the glass comprises 17.5-19.0 wt.-% $K_2O$.

7. The composition according to claim 1, wherein the glass comprises at least one of the components in the following amount(s), in weight percent:

| | |
|---|---|
| SiO$_2$ | 64.0-65.0% |
| K$_2$O | 18.0-18.5% |
| Al$_2$O$_3$ | 10.0-10.5% |
| Li$_2$O | 2.0-2.1% |
| MgO | 0.4-2.1% |
| CaO | 1.9-2.3% |
| ZrO$_2$ | 1.0-2.4% |
| CeO$_2$ | 0.4-0.8%. |

8. The composition according to claim 7, wherein the glass comprises at least one of the components in the following amount(s), in weight percent:

| | |
|---|---|
| MgO | 0.4-0.7% |
| CaO | 1.9-2.1% |
| ZrO$_2$ | 2.0-2.4%. |

9. The composition according to claim 1, having a firing temperature of 900 to 950° C.

10. The composition according to claim 9, having a liring temperature of 910° C. to 930° C.

11. The composition according to claim 1, which has a linear coefficient of thermal expansion of 8.4 to 9.1×10$^{-6}$ K$^{-1}$ in the temperature range of 100 to 500° C.

12. A glazing material for dental restorations comprising the composition of claim 1.

13. In combination, the glazing material of claim 12, and a dental restoration, wherein the dental restoration is a bridge, a crown, an inlay, an onlay, a veneer, a cap, or a part thereof.

14. The combination according to claim 13, wherein the dental restoration comprises a glass, a ceramic, a metal or a glass-ceramic framework.

15. The combination according to claim 14, wherein the glass-ceramic is a lithium silicate glass-ceramic, a mica glass-ceramic or a chondrodite glass-ceramic.

16. The combination according to claim 15, wherein the lithium silicate glass-ceramic is a lithium metasilicate or a lithium disilicate glass-ceramic.

17. A process of applying a glaze onto a dental restoration, the process comprising:
(a) applying the composition according to claim 1 onto the dental restoration; and
(b) thermally treating the dental restoration and the applied composition in a manner which transforms the glass into a glaze that adheres firmly to the restoration.

18. The process according to claim 17, wherein the thermal treatment takes place at a temperature of at least 860° C.

19. The process according to claim 18, wherein the thermal treatment takes place at a temperature of 860° C.-960° C.

20. The process according to claim 17, wherein the dental restoration is based on a glass, a ceramic, a metal or a glass-ceramic.

21. The process according to claim 20, wherein the thermal treatment also leads to the formation of crystals in the glass or the glass-ceramic.

22. The process according to claim 21, wherein the thermal treatment leads to the formation of lithium disilicate crystals or mica crystals.

23. The process according to claim 21, in which the formation of crystals brings about an increase in the strength of the dental restoration.

24. The glazing material according to claim 12 further comprising a glaze, a staining dye or a mixture thereof.

25. The process according to claim 17 wherein the composition of step (a) is mixed with a glaze, a staining dye or a mixture thereof prior to applying onto the dental restoration.

26. A glazing material for dental restorations comprising the following components, in weight percent:

| | |
|---|---|
| SiO$_2$ | 60.0-65.0% |
| K$_2$O | 15.0-19.0% |
| Al$_2$O$_3$ | 6.0-10.5% |
| Li$_2$O | 1.8-2.2% |
| Me$^{II}$O | 2.5-8.5% |
| further oxides | 1.5-7.0% | wherein
(a) Me$^{II}$O represents at least one divalent oxide which is selected from the group of the oxides of Ca, Mg, Sr and Zn, wherein ZnO is present in an amount less than 2.0%: and
(b) further oxides represents at least one oxide which is selected from the group of the oxides of B, Zr, Ce and Y; and
wherein the glass has a linear coefficient of thermal expansion of 8.0 to 9.5×10$^{-6}$ K$^{-1}$ in the temperature range of 100 to 500° C.

27. In combination, the glazing material of claim 26, and a dental restoration, wherein the dental restoration is a bridge, a crown, an inlay, an onlay, a veneer, a cap, or a part thereof.

28. The combination according to claim 27, wherein the dental restoration comprises a glass, a ceramic, a metal or a glass-ceramic framework.

29. The combination according to claim 28, wherein the glass-ceramic is a lithium silicate glass-ceramic, a mica glass-ceramic or a chondrodite glass-ceramic.

30. The combination according to claim 29, wherein the lithium silicate glass-ceramic is a lithium metasilicate or a lithium disilicate glass-ceramic.

31. The glazing material according to claim 26 further comprising a glaze, a staining dye or a combination thereof.

32. A process of applying a glaze onto a dental restoration, the process comprising:
(a) applying onto the dental restoration; the composition comprising the following components, in weight percent:

| | |
|---|---|
| SiO$_2$ | 60.0-65.0% |
| K$_2$O | 15.0-19.0% |
| Al$_2$O$_3$ | 6.0-10.5% |
| Li$_2$O | 1.8-2.2% |
| Me$^{II}$O | 2.5-8.5% |
| further oxides | 1.5-7.0% | wherein
(i) Me$^{II}$O represents at least one divalent oxide which is selected from the group of the oxides of Ca, Mg, Sr and Zn, wherein ZnO is present in an amount less than 2.0%: and
(ii) further oxides represents at least one oxide which is selected from the group of the oxides of B, Zr, Ce and Y; and
wherein the glass has a linear coefficient of thermal expansion of 8.0 to 9.5×10$^{-6}$ K$^{31}$ in the temperature range of 100 to 500° C.; and
(b) thermally treating the dental restoration and the applied composition in a manner which transforms the glass into a glaze that adheres firmly to the restoration.

33. The process according to claim 32. wherein the thermal treatment takes place at a temperature of at least 860° C.

34. The process according to claim 33, wherein the thermal treatment takes place at a temperature of 860° C.-960° C.

35. The process according to claim 32, wherein the dental restoration is based on a glass, a ceramic, a metal or a glass-ceramic.

36. The process according to claim 35. wherein the thermal treatment also leads to the formation of crystals in the glass or the glass-ceramic.

37. The process according to claim 36, wherein the thermal treatment leads to the formation of lithium disilicate crystals or mica crystals.

38. The process according to claim 36, in which the formation of crystals brings about an increase in the strength of the dental restoration.

39. The process according to claim 32 wherein the composition of step (a) is mixed with a glaze, a staining dye or a mixture thereof prior to applying onto the dental restoration.

\* \* \* \* \*

UNITED STATES PATENT AND TRADEMARK OFFICE
CERTIFICATE OF CORRECTION

PATENT NO. : 7,674,736 B2  Page 1 of 1
APPLICATION NO. : 11/798172
DATED : March 9, 2010
INVENTOR(S) : Diana Tauch, Harald Burke and Volker M. Rheinberger It is certified that error appears in the above-identified patent and that said Letters Patent is hereby corrected as shown below:

Column 9, line 23, please delete "liring" and insert --firing--

Column 9, line 24, please delete "of910" and insert --of 910--

Column 9, line 24, please delete "C. to" and insert --C to--

Column 9, line 26, please delete "of8.4" and insert --of 8.4--

Column 9, line 53, please delete "C. 960" and insert --C 960--

Column 10, line 58, please delete "2.0%:" and insert --2.0%;--

Column 10, line 63, please delete "K31" and insert --K-1--

Column 10, line 64, please delete "C.;" and insert --C;--

Column 11, line 4, please delete "C." and insert --C--

Signed and Sealed this

Twenty-seventh Day of April, 2010

David J. Kappos
*Director of the United States Patent and Trademark Office*